United States Patent [19]

Al-Damluji

[11] Patent Number: 5,240,930
[45] Date of Patent: Aug. 31, 1993

[54] PHARMACEUTICAL COMPOSITIONS FOR TREATMENT OF DEPRESSION AND LOW BLOOD PRESSURE

[75] Inventor: Saad Al-Damluji, London, England

[73] Assignee: National Research Development Corporation, London, England

[21] Appl. No.: 659,229

[22] Filed: Feb. 22, 1991

Related U.S. Application Data

[62] Division of Ser. No. 348,589, Apr. 28, 1989, Pat. No. 5,015,654.

[30] Foreign Application Priority Data

Sep. 2, 1987 [GB] United Kingdom ............... 8720600

[51] Int. Cl.$^5$ ................ A61K 31/44; A61K 31/415; A61K 31/13
[52] U.S. Cl. ................ 514/280; 514/402; 514/561; 514/929; 514/411
[58] Field of Search .............. 514/280, 410, 411, 564, 514/970, 929

[56] References Cited

FOREIGN PATENT DOCUMENTS 2068376B 8/1981 United Kingdom .

OTHER PUBLICATIONS

CA:111 No. 167239g-Hsu et al.
CA:107 No. 162048 b-Nishino, et al.
Al-Damluji et al., *J. Endocrinol. Invest.*, 10 (Suppl. 3), 1987.
Al-Damluji et al., *British J. Pharmacol.*, (1988) 95, 405-412.
Al-Damluji et al., *J. Endocrinol.*, Supplement 117; presented at 7th joint meeting of British Endocrine Societies, Executer, Apr. 18-21, 1988.
Al-Damluji et al., "Activation of Endogenous Catecholamines Stimulates ACTH Secretion in Man," 8th Int. Congress of Endocrin., Kyoto, Japan, Jul. 17-23, 1988.

*Primary Examiner*—S. J. Friedman
*Assistant Examiner*—T. J. Criares
*Attorney, Agent, or Firm*—Bacon & Thomas

[57] ABSTRACT

A pharmaceutical composition which comprises a mixture of an alpha-2 adrenoceptor antagonist, preferably idazoxan, or a pharmaceutically acceptable salt thereof, and either a catecholamine precursor or an inhibitor of aromatic L-amino acid decarboxylase, preferably carbidopa. The compositions can be used for treatment of endogenous depression or low blood pressure.

18 Claims, 1 Drawing Sheet

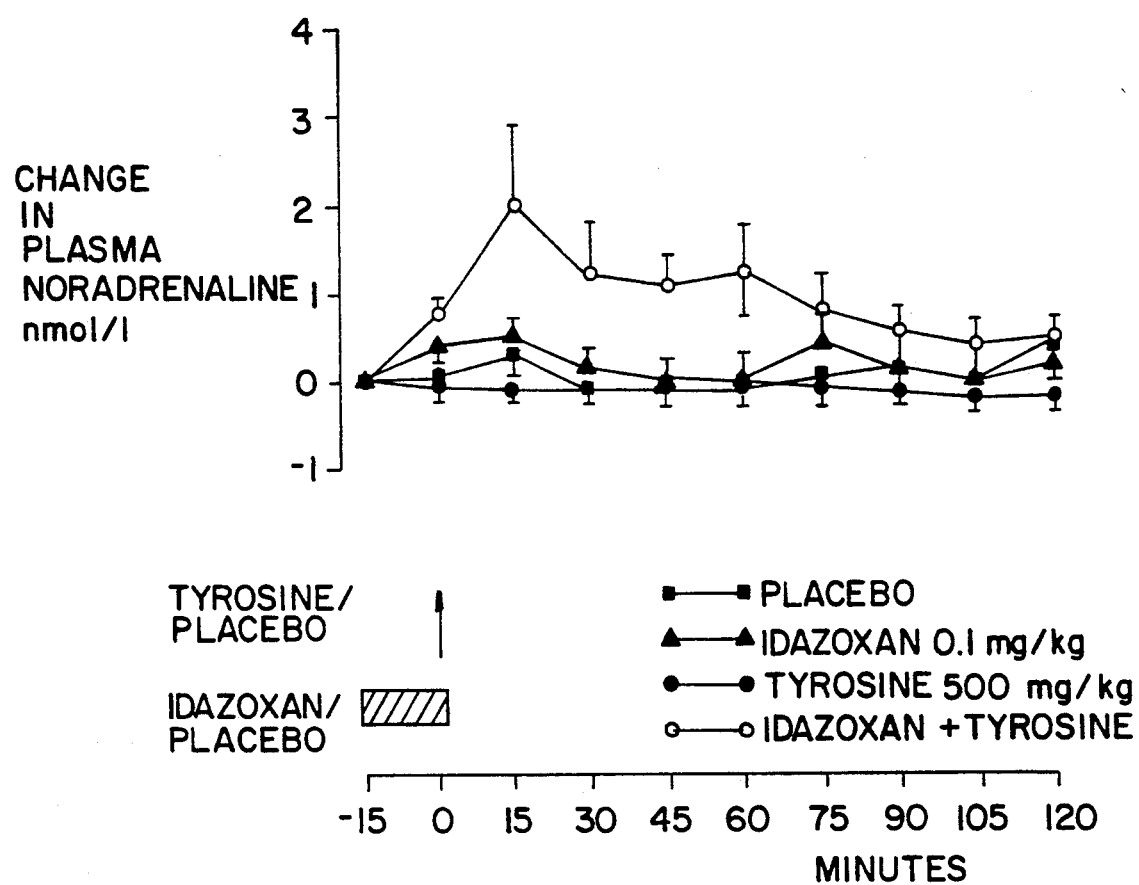

PHARMACEUTICAL COMPOSITIONS FOR TREATMENT OF DEPRESSION AND LOW BLOOD PRESSURE

This application is a division of allowed U.S. patent application Ser. No. 07/348,589 filed Apr. 28, 1989, now U.S. Pat. No. 5,015,654.

This invention relates to pharmaceutical compositions.

Adrenaline and noradrenaline are substances that are released from nerve endings in the brain and in the periphery, and from the adrenal glands. They act as chemical messengers or 'neurotransmitters'. Adrenaline, noradrenaline and a related substance, dopamine, belong to a class of chemicals known as the catecholamines. They are synthesised in the body from the amino acid tyrosine. Tyrosine is a natural dietary amino acid, but the body can also synthesise tyrosine from the amino acid phenylalanine. Tyrosine is converted into dihydroxyphenylalanine, which is in turn converted to dopamine, noradrenaline, and finally to adrenaline.

Adrenergic receptors (usually known as adrenoceptors) are the sites of action of adrenaline and noradrenaline. They mediate physiological or pharmacological effects upon stimulation by an appropriate chemical, be it an endogenous substance or a synthetic drug with similar activity (agonist drug). By using a variety of pharmacological techniques, these receptors have been classified into alpha and beta adrenoceptors. Alpha adrenoceptors have in turn been subdivided into alpha-1 and alpha-2 adrenoceptor subtypes. Alpha-2 adrenoceptors are located in the membranes both of the target cells for adrenaline and noradrenaline (known as post synaptic alpha-2 adrenoceptors), and in the noradrenergic neurones themselves (known as presynaptic alpha-2 adrenoceptors). The presynaptic alpha-2 adrenoceptors inhibit the release of noradrenaline from its nerve terminals and act as a 'negative feedback' mechanism following the release of noradrenaline from its nerve terminals. Thus, stimulation of alpha-2 adrenoceptors by agonists, including the endogenous neurotransmitters adrenaline and noradrenaline, reduces the amount of neurotransmitter released from the neuron. Conversely, administration of an alpha-2 adrenoceptor antagonist drug will increase the amount of neurotransmitter released from the neuron, by blocking the presynaptic alpha-2 adrenoceptors. Alpha-2 adrenoceptor antagonists are currently being investigated for a possible therapeutic effect in illnesses that are believed to be associated with reduced noradrenaline activity, such as endogenous depression. It has also been proposed that alpha-2 adrenoceptor antagonists may be therapeutically useful in the treatment of low blood pressure states, by increasing the output of noradrenaline, which increases the blood pressure.

One of the most effective alpha-2 adrenoceptor antagonists is idazoxan which has been developed by Reckitt & Colman Pharmaceutical Division; this drug is described and claimed in GB-B-2068376, which is incorporated herein by reference.

The present invention is based upon the surprising discovery that the effectiveness of an alpha-2 adrenoceptor antagonist in causing noradrenaline release from nerve endings is enhanced significantly by administration of a catecholamine precursor to increase the amount of catecholamine that is available for release from the neuron.

Accordingly the present invention provides a pharmaceutical composition for the treatment of depression and/or low blood pressure which comprises a mixture of an alpha-2 adrenoceptor antagonist, preferably idazoxan, or a pharmaceutically acceptable salt thereof, and either a catecholamine precursor or an inhibitor of aromatic L-amino acid decarboxylase.

Preferably the composition comprises a catecholamine precursor and an inhibitor of aromatic amino acid decarboxylase.

In the treatment of depression, the oral route of administration is preferable in view of the long term nature of this condition and the requirement for prolonged therapy. However, under some circumstances administration by injection of a single or repeated doses of the antidepressant drug is desirable. This may be so if it is important to attain adequate blood level of the drugs rapidly, or if a patient is unable to take the drug orally.

In the treatment of low blood pressure states, the intravenous route of administration is preferable, as a rapid response is usually desirable.

In one of the aspects the invention provides a composition wherein the risk of side effects from alpha-2 adrenoceptor antagonists is reduced by the addition of a compound that inhibits the synthesis of the catecholamine neurotransmitters in the peripheral nervous system, but not in the brain. The increased output of noradrenaline in the periphery caused by alpha-2 adrenoceptor antagonists results in elevation of blood pressure, awareness of heart beat and sweating. These effects can be reduced or eliminated by compounds which inhibit the aromatic L-amino acid decarboxylase enzyme. Aromatic L-amino acid decarboxylase is an enzyme that is widely distributed in the body, including the brain (Lovenberg et al, 1962, The Journal of Biological Chemistry, 237, 89). In catecholamine neurons, it catalyses the conversion of L-dihydroxyphenylalanine (L-DOPA) to L-dihydroxyphenylethylamine (dopamine), so it is sometimes known by its trivial name, 'DOPA decarboxylase'. The decarboxylation of L-DOPA is one of the steps in the synthesis of the catecholamine neurotransmitters (dopamine, noradrenaline and adrenaline) from tyrosine. Inhibition of this enzymatic step results in a fall in the rate of synthesis of the catecholamine neurotransmitters. Several compounds have been described with the ability to inhibit this enzyme. These include carbidopa (alpha-methyl-L-DOPA hydrazine), benserazide (N-[DL-seryl]-N'-[2,3,4-trihydroxybenzyl]-hydrazine), NSD 1015 (m-hydroxybenzylhydrazine) and MK 485 (beta-[3,4-dihydroxyphenyl]-alphahydrazino-alpha-methyl propionic acid). Some of these inhibitory compounds, such as carbidopa and MK 485 do not reach the brain following peripheral administration, even when given in apparently large doses. Other compounds, such as benserazide, only reach the brain when given in large doses (Bartholini & Pletscher, 1969, Journal of Pharmacy & Pharmacology, 21, 323). It follows that using a compound such as carbidopa, it is possible to inhibit the synthesis of the catecholamine neurotransmitters in the peripheral sympathetic nervous system without affecting the equivalent process in the brain (Wurtman & Watkins, 1977, Nature, 265, 79). The peripheral effects of alpha-2 adrenoceptor antagonists, alone or in combination with catecholamine precursors, can be reduced or abolished by these aromatic L-amino acid decarboxylase inhibitors. A particularly preferred decarboxylase inhibitor for use in the composition of the invention is carbidopa although appropriate doses of benserazide, and MK 485 may also be used.

Several classes of drugs have been described with alpha-2 adrenoceptor antagonist activity and any of these may be used in compositions according to this invention; these include:

1. Imidazole derivatives such as Idazoxan (RX 781094) which acts as a competitive antagonist at alpha-2 adrenoceptors. Its pharmacological characteristics make it one of the most highly selective of the available antagonists at alpha-2 adrenoceptors; the drug has minimal activity at alpha-1 adrenoceptors and no significant activity at beta adrenergic, opiate, histaminergic, cholinergic and serotonergic receptors (Doxey, JC et al, 1983, British Journal of Pharmacology, 78, 489). Idazoxan increases noradrenaline release from neurons in the brain and in the periphery following oral administration. Idazoxan is currently undergoing clinical trials as an antidepressant. It is available for investigative use as a solution for intravenous injection (10 mg per ampoule) and as tablets containing 5, 10, 20 and 40 mg of the drug. Several other derivatives and analogues have alpha-2 adrenoceptors antagonists activity, including imiloxan (RS 21361; Doxey, JC et al, 1983, British Journal of Pharmacology, 78, 489), the 2-methoxy analogue of idazoxan (RX 821002) (Doxey, JC et al, 1984, British Journal of Pharmacology, 81, 181P), the 2-isoprenyl analogue (RX 811005) (Doxey et al, 1984, British Journal of Pharmcology, 83, 713,) the 2-ethyl analogue (RX 811033) (Gadie, B et al, 1984, British Journal of Pharmacology, 83, 707), the dihydrofuran ring substituted analogue S 9871 (Joly, G et al, 1984, Archives Internationales Pharmacodynamie & Therapie, 269, 277) and the dihydrobenzofuranyl analogue (Chapleo CB, et al, 1984, Journal of Medicinal Chemistry, 27, 570) ([imidazolinyl-2-]-2 dihydro 2,3 benzofurane).

2. The quadricyclic compound mianserin is an established antidepressant in clinical practice. It has prominent alpha-2 adrenoceptor antagonist activity, but in addition, it is active at receptors for serotonin and histamine. Several derivatives of mianserin possess alpha-2 adrenoceptor antagonist activity, including desmethylmianserin (Nickolson, V. J. et al, 1982, Archives of Pharmacology, 319, 48), 8-hydroxymianserin (Nickolson et al, 1982, Archives of Pharmacology, 319, 48), S (+)-mianserin (Nickolson, V. J. & Wieringa, J. H., 1981, Journal of Pharmacy and Pharmacology, 33, 760), the 6-aza analogue Org-3770 (Nickolson, V. J. et al, 1982, Archives of Pharmacology, 319, 48), aptazapine (Nickolson, V. J. & Wieringa, J. H., 1981, Journal of Pharmacy & Pharmacology, 33, 760), CGS-7525A (1,3,4,14b-tetrahydro-2-methyl-10H-pyrazino-[1,2-a]pyrrolo[2,1-c][1,4]benzodiazepine maleate) (Liebman, J. M. et al, 1983, Life Sciences, 32, 355), 1(3-fluoro-2-pyridinyl) piperazine, its methyl derivative (Saari, W. S. et al, 1983, Journal of Medicinal Chemistry, 26, 1696) and 4-(3-fluoro-2-pyridinyl)-1,2,5,6-tetrahydropyridine (Saari, W. S. et al, 1984, Journal of Medicinal Chemistry, 27, 1182).

3. Yohimbine is an indole derivative found in a variety of plants. It has several pharmacological actions including alpha-2 adrenoceptor antagonist activity, as does its derivative rauwolscine.

4. The newly synthesised benzoquinolizine drugs from Wyeth Laboratories Wy 26703, N-((2β,11bα)-1,3,4,6,7,11b-hexahydro-2H-benzo(a)quinolizin-2-yl)-N-methylisobutanesulphonamide, hydrochloride) and WY 26392 (N-((2β,11bα)-1,3,4,6,7,11b-hexahydro-2H-benzo-(a)-quinolizin-2-yl)-N-methylpropanesulphonamide, hydrochloride) and WY25309 (N-((2β,11bα)-1,3,4,6,7,11b-hexahydro-2H-benzo(a)quinolizin-2-yl)-N-methylmethanesulphonamide hydrochloride), have been reported to have alpha-2 adrenoceptor antagonist activity (Paciorek, P. M. et al, 1984, British Journal of Pharmacology, 82, 127).

5. The azepine compounds B-HT-958(2-amino-6-(p-chlorobenzyl)-4H-5,6,7,8-tetrahydro-thiazolozepine)[5,4-d]azepine) (Hortnagl, H. et al, 1984, European Journal of Pharmacology, 106, 335) and SK & F 86466 (6-chloro-2,3,4,5-tetrahydro-3-methyl1H-3-benzazepine; DeMarinis, R. M. et al, 1983, Journal of Medicinal Chemistry, 26, 1213) also possess alpha-2 adrenoceptor antagonist activity.

The following are examples of pharmaceutical compositions according to the invention. It is to be understood however that apart from the alternative alpha-2 adrenoceptor antagonists listed below other aromatic L-amino acid decarboxylase inhibitors may be substituted for carbidopa. Benserazide, 100 mg, is a particularly suitable substitute for carbidopa in the following compositions.

1. ORAL MIXTURES

A. Phenylalanine 30 grams, idazoxan 40 milligrams and optionally carbidopa 25 milligrams.

B. Tyrosine 30 grams, idazoxan 40 milligrams, and optionally carbidopa 25 milligrams.

C. Dihydroxyphenylalanine 500 milligrams, idazoxan 40 milligrams and optionally carbidopa 25 milligrams.

D. Phenylalanine 30 grams, mianserin 30 milligrams and optionally carbidopa 25 milligrams.

E. Tyrosine 30 grams, mianserin 30 milligrams and carbidopa 25 milligrams.

F. Dihydroxyphenylalanine 500 milligrams, mianserin 30 milligrams and carbidopa 25 milligrams.

G. Phenylalanine 30 grams, Org-3770 60 milligrams and carbidopa 25 milligrams.

H. Tyrosine 30 grams, Org-3770 60 milligrams and carbidopa 25 milligrams.

I. Dihydroxyphenylalanine 500 milligrams, Org-3770 60 milligrams and carbidopa 25 milligrams.

J. Phenylalanine 30 grams, yohimbine 10 milligrams and carbidopa 25 milligrams.

K. Tyrosine 30 grams, yohimbine 10 milligrams and carbidopa 25 milligrams.

L. Dihydroxyphenylalanine 500 milligrams, yohimbine 10 milligrams and carbidopa 25 milligrams.

2. INJECTABLE MIXTURES

A. Phenylalanine 500 milligrams and idazoxan 10 milligrams.

B. Tyrosine 500 milligrams and idazoxan 10 milligrams.

C. Dihyroxyphenylalanine 50 milligrams and idazoxan 10 milligrams.

D. Dopamine 200 milligrams and idazoxan 10 milligrams.

E. Phenylalanine 500 milligrams and Org-3770 5 milligrams.

F. Tyrosine 500 milligrams and Org-3770 5 milligrams.

G. Dihydroxyphenylalanine 50 milligrams and Org-3770 5 milligrams.

H. Dopamine 200 milligrams and Org-3770 5 milligrams.

I. L-dihydroxyphenylserine 200 milligrams and Org-3770 5 milligrams.

L-dihydroxyphenylserine is a synthetic catecholamine precursor and it is to be understood that other such precursors may be used in the compositions of this invention.

The oral and injectable mixtures disclosed above will be used in practice with excipients, diluents, carriers or the like. The pharmaceutical compositions may be in the form suitable for oral, rectal or parenteral administration. Such oral compositions may be in the form of capsules, tablets, granules or liquid preparations, such as elixirs, syrups or suspensions. A tablet may comprise as well as the essential ingredients described above an inert diluent such as calcium phosphate, microcrystalline cellulose, lactose, sucrose or dextrose; granulating and disintegrating agents such as starch; binding agents such as starch, gelatine, polyvinyl polyvinylpyrrolidone or acacia; and lubricating agents such as magnesium stearate, stearic acid or talc.

Compositions in the form of capsules may contain a compound effective as an antagonist at the alpha-2 adrenoceptor or, where appropriate, a pharmaceutically acceptable salt thereof, mixed with an inert solid diluent such as calcium phosphate, lactose or kaolin in a hard gelatine capsule.

Compositions for parenteral administration may be in the form of sterile injectable preparations, such as solutions or suspensions in, for example, water, saline or 1,3-butanediol.

Where the alpha-2 adrenoceptor antagonist is idazoxan, the unit dosage form for all administrations may contain from 1 to 200 mg preferably from 10 to 50 mg of the active ingredient; for this drug a parenteral unit dosage form may contain from 0.1 to 10 mg of the drug per 1 ml of the preparation.

In the case of a sole unit dosage form containing from 5 to 40 mg of the alpha-2 adrenoceptor antagonist, the composition may also contain from 250 mg to 40 g of the catecholoamine precursor.

It has been indicated above that, in the case where it is desired not to increase the blood pressure of a patient, the composition also contains an aromatic L-amino acid decarboxylase inhibitor such as carbidopa, and this may be present in a weight ratio relative to the alpha-2 adrenoceptor antagonist of from 2:1 to 1:4, preferably from 1.5:1 to 1:2. It is preferred that an injectable unit dosage form contains from 5 to 15 mg of the alpha-2 adrenoceptor antagonist and from 50 to 750 mg of the catecholamine precursor, which is preferably tyrosine.

The present invention also includes compositions comprising an alpha-2 adrenoceptor antagonist as described above or a pharmaceutically acceptable salt thereof and an aromatic L-amino acid decarboxylase inhibitor only. From the above it will be clear that a combination of an aromatic L-amino acid decarboxylase inhibitor such as carbidopa, and an alpha-2 adrenoceptor antagonist, such as idazoxan is a beneficial one.

In such a composition the ratio of alpha-2 adrenoceptor antagonist to carbidopa is preferably from 2:1 to 1:4, more preferably from 1.5:1 to 1:2.

The following are examples of pharmaceutical compositions according to this aspect of the invention.

I. Idazoxan 40 milligrams, carbidopa 25 milligrams, and optionally phenylalanine 30 grams.

II. Idazoxan 40 milligrams, carbidopa 25 milligrams, and optionally tyrosine 30 grams.

III. Idazoxan 40 milligrams, carbidopa 25 milligrams, and optionally dihydroxyphenylalanine 30 grams.

IV. Mianserin 30 milligrams, carbidopa 25 milligrams and optionally phenylalanine 30 grams.

V. Mianserin 30 milligrams, carbidopa 25 milligrams and optionally tyrosine 30 grams.

VI. Mianserin 30 milligrams, carbidopa 25 milligrams and optionally dihydroxyphenylalanine 500 milligrams.

VII. Org-3770 60 milligrams, carbidopa 25 milligrams and optionally phenylalanine 30 grams.

VIII. Org-3770 60 milligrams, carbidopa 25 milligrams and optionally tyrosine 30 grams.

IX. Org-3770 60 milligrams, carbidopa 25 milligrams and optionally dihydroxyphenylalanine 30 grams.

X. Yohimbine 10 milligrams, carbidopa 25 milligrams and optionally phenylalanine 30 grams.

XI. Yohimbine 10 milligrams, carbidopa 25 milligrams and optionally tyrosine 30 grams.

XII. Yohimbine 10 milligrams, carbidopa 25 milligrams and optionally dihydroxyphenylalanine 30 grams.

Since only the L-form of an amino acid is physiologically active, those skilled in the art will understand that the catecholamine precursors incorporated with the compositions of the invention have to be in the L-form or alternatively, providing an appropriate concentration adjustment is made, mixtures of the D and L forms.

The advantageous effects of a combination of treatment with an alpha-2 adrenoceptor antagonist and a catecholamine precursor on a) plasma noradrenaline concentrations and b) blood pressure, are demonstrated by way of the following clinical data.

Seven normal men were studied on 4 occasions each, receiving:
1) idazoxan 0.1 mg/kg intravenously over 12.5 minutes, followed by tyrosine 500 mg/kg orally;
2) 0.15M saline (placebo) intravenously followed by tyrosine 500 mg/kg orally;
3) idazoxan (0.1 mg/kg intravenously) followed by placebo (calcium carbonate) orally;
4) 0.15M saline intravenously followed by calcium carbonate orally.

Idazoxan was dissolved in 0.15M saline 0.1 mg/kg, and the same volume of normal saline was administered as a placebo. Tyrosine and calcium carbonate were given as an emulsion in 150 mls of water orally. The drugs were administered in double blind, random order at intervals of one week. The subjects were studies in the recumbent position in a quiet room and blood samples were taken at 15 minute intervals. Heart rate was calculated from the electrocardiogram and blood pressure was measured by sphygmomanometry. Plasma noradrenaline concentrations were measured by high performance liquid chromatography followed by electrochemical detection. Statistical comparisons were made by analysis of variance of changes in the area under the curve from the value at the −15 minute time point.

DESCRIPTION OF DRAWING

The result of the noradrenaline concentration measurements are shown in FIG. 1.

Idazoxan and tyrosine had no effect on plasma noradrenaline concentrations when they were administered on their own. In contrast, the combined administration of tyrosine and idazoxan increased the plasma concentration of noradrenaline in comparison to placebo. The increment in plasma noradrenaline concentrations was statistically significant (P<0.01).

In the above procedure the effect of placebo, tyrosine 500 mg/kg orally, idazoxan 0.1 mg/kg intravenously and the combination of tyrosine and idazoxan in the above doses on systolic blood pressure in seven normal men was determined. The data are expressed in Table 1 as the means ± standard errors of the mean.

TABLE 1

CHANGE IN SYSTOLIC BLOOD PRESSURE
(60 MINUTE - BASELINE)

| DRUG | |
|---|---|
| Placebo + placebo | −1.7 ± 1.7 mm mercury |
| Tyrosine + placebo | +2.3 ± 2.0 mm mercury |
| Idazoxan + placebo | +7.3 ± 2.1 mm mercury |
| Idazoxan + tyrosine | +10.7 ± 0.4 mm mercury |

Idazoxan caused small but significant increases in systolic blood pressure in comparison to placebo, both when it was given alone and in combination with tyrosine (P<0.001), as shown in Table 1.

The increase in plasma noradrenaline concentrations and elevation of blood pressure indicate an increase in the rate of release of noradrenaline from the neurones of the peripheral sympathetic nervous system. These data demonstrate that the addition of a catecholamine precursor, tyrosine, enhances the action of an alpha-2 adrenoceptor antagonist.

I claim:

1. A pharmaceutical composition which comprises a mixture of a therapeutically effective amount of an alpha-2 adrenoceptor antagonist which is an indole derivative selected from the group consisting of yohimbine and derivatives thereof and a therapeutically effective amount of a catecholamine precursor which is a member selected from the group consisting of tyrosine, phenylalanine, dihydroxyphenylalanine, dopamine and L-dihydroxyphenylserine.

2. A composition as claimed in claim 1 which additionally comprises an inhibitor of aromatic L-amino acid decarboxylase which is a member selected from the group consisting of carbidopa, benserazide, m-hydroxybenzylhydrazine, and beta -alphahydrazino-alpha-methyl-propionic acid.

3. A composition as claimed in claim 1 wherein there is also present a pharmaceutically acceptable diluent or carrier.

4. A composition as claimed in claim 1 which is in unit dosage form.

5. A composition as claimed in claim 4 wherein each unit dosage contains from 1 to 200 mg of alpha-2 adrenoceptor antagonist.

6. A composition as claimed in claim 1 wherein the catecholamine precursor is tyrosine, phenylalanine, dihydroxyphenylalanine, or dopamine.

7. A composition as claimed in claim 4 wherein the solid unit dosage form contains from 5 to 40 mg of the alpha-2 adrenoceptor antagonist and 250 mg to 40 g of the catecholamine precursor.

8. A composition as claimed in claim 7 wherein the composition contains carbidopa in a weight ratio relative to the alpha-2 adrenoceptor antagonist of from 2:1 to 1:4.

9. A composition as claimed in claim 4 wherein the injectable unit dosage form contains from 5 to 15 milligrams of the alpha-2 adrenoceptor antagonist and from 50 to 750 mg of the catecholamine precursor.

10. A pharmaceutical composition as claimed in claim 1, wherein said alpha-2 adrenoceptor antagonist is yohimbine.

11. A pharmaceutical composition as claimed in claim 10, wherein said catecholamine precursor is phenylalanine.

12. A pharmaceutical composition as claimed in claim 2, wherein said alpha-2 adrenoceptor antagonist is yohimbine, said catecholamine precursor is phenylalanine and said inhibitor of aromatic L-amino acid decarboxylase is carbidopa.

13. A pharmaceutical composition as claimed in claim 1, wherein said alpha-2 adrenoceptor antagonist is rauwolscine.

14. A pharmaceutical composition as claimed in claim 1, wherein the catecholamine precursor is a member selected from the group consisting of tyrosine, phenylalanine, dihydroxyphenylalanine and dopamine.

15. A pharmaceutical composition as claimed in claim 2, wherein said inhibitor of aromatic L-amino acid decarboxylase is carbidopa.

16. The method of treatment of low blood pressure which comprises administering to a person requiring treatment a therapeutically effective amount of the pharmaceutical composition as claimed in claim 1.

17. A method of treatment of endogenous depression which comprises administering to persons requiring treatment a therapeutically effective amount of the pharmaceutical composition as claimed in claim 1.

18. A method of treatment of endogenous depression which comprises administering to a person requiring treatment a therapeutically effective amount of the pharmaceutical composition as claimed in claim 2.

* * * * *

UNITED STATES PATENT AND TRADEMARK OFFICE
CERTIFICATE OF CORRECTION

PATENT NO. : 5,240,930
DATED : Aug. 31, 1993
INVENTOR(S) : Saad Al-Damluji

It is certified that error appears in the above-identified patent and that said Letters Patent is hereby corrected as shown below:

Column 7,

Claim 2, line 5, change "beta -alphahydrazino-alpha-" to
-- beta-[3,4-dihydroxyphenyl]-alphahydrazino-alpha- --.

Col. 8, claim 14, line 2, change "1" to --10--

Signed and Sealed this

Twenty-fourth Day of May, 1994

Attest:

BRUCE LEHMAN

Attesting Officer        Commissioner of Patents and Trademarks